United States Patent [19]
Wegner et al.

[11] Patent Number: 5,468,366
[45] Date of Patent: Nov. 21, 1995

[54] COLLOIDAL-GOLD ELECTROSENSOR MEASURING DEVICE

[75] Inventors: Steven Wegner, Chapel Hill; Michael A. Harpold; Terence M. McCaffrey, both of Durham; Susan E. Morris, Chapel Hill; Marek Wojciechowski, Cary; Junguo Zhao, Chapel Hill; Robert W. Henkens; Najih Naser, both of Durham; John P. O'Daly, Carrboro, all of N.C.

[73] Assignee: Andcare, Inc., Durham, N.C.

[21] Appl. No.: 316,433

[22] Filed: Sep. 30, 1994

Related U.S. Application Data

[63] Continuation-in-part of Ser. No. 73,806, Jun. 7, 1993, Pat. No. 5,368,707, which is a continuation-in-part of Ser. No. 821,732, Jan. 15, 1992, Pat. No. 5,217,594.

[51] Int. Cl.$^6$ .................................................. G01N 27/26
[52] U.S. Cl. ................. 204/403; 204/153.12; 204/153.1; 204/412; 204/415; 204/435; 435/817; 435/287.1; 436/74; 436/77
[58] Field of Search ...................... 204/403, 412, 204/415, 435, 153.12, 153.1; 435/817, 288; 436/74, 77

[56] References Cited

U.S. PATENT DOCUMENTS

| | | | |
|---|---|---|---|
| 4,090,926 | 5/1978 | Matson | 204/1 T |
| 4,374,041 | 2/1983 | Matson | 436/60 |
| 4,581,336 | 4/1986 | Malloy et al. | 435/176 |
| 4,820,399 | 4/1989 | Senda et al. | 204/403 |
| 4,950,378 | 8/1990 | Nagata | 204/402 |
| 4,970,145 | 11/1990 | Bennetto et al. | 435/817 |
| 5,160,418 | 11/1992 | Mullen | 204/153.12 |
| 5,217,594 | 6/1993 | Henkens et al. | 204/403 |
| 5,225,064 | 7/1993 | Henkens et al. | 204/403 |
| 5,284,567 | 2/1994 | Matson | 204/153.12 |
| 5,292,423 | 3/1994 | Wang | 204/434 |
| 5,368,707 | 11/1994 | Kenkens et al. | 204/153.12 |
| 5,391,272 | 2/1995 | O'Daly et al. | 204/403 |

FOREIGN PATENT DOCUMENTS

WO87/07295 12/1987 WIPO.
WO91/17259 11/1991 WIPO.

OTHER PUBLICATIONS

Albery et al., "Inhibited Enzyme Electrodes. Part 3.," *Biosensors & Bioelectronics*, 5:397–413, 1990, published in Great Britain, no month available.

Almestrand et al., "Determination of Lead in Whole Blood with a Simple Flow–Injection System and Computerized Stripping Potentiometry," *Analytica Chimica Acta*, 209:339–343, 1988, published in The Netherlands, no month available.

Baum & Czok, "Enzymatische Bestimmung von, 'ionisiertem' Magnesium im Plasma," *Biochemische Zeitschrift*, 332:121–130, 1959, no month available.

Botré et al., "Synthesis and Inhibitory Activity on Carbonic Anhydrase of Some New Sulpiride Analogues Studied by Means of a New Method," *Journal of Medicinal Chemistry*, 29:1814–1020, 1986, no month available.

"New Rules Set for Blood Lead Levels," *Chemical and Engineering News*, p. 17, Oct. 14, 1991.

Fair & Jamieson, "Studies of Protein Adsorption on Polystyrene Latex Surfaces," *Journal of Colloid and Interface Science*, 77(2):525–534, 1980, no month available.

(List continued on next page.)

*Primary Examiner*—John Niebling
*Assistant Examiner*—Bruce F. Bell
*Attorney, Agent, or Firm*—Arnold, White & Durkee

[57] ABSTRACT

The present invention provides a new device for use in measuring lead levels in biological and environmental samples. Using square wave coulometry and colloidal gold particles impregnated on carbon electrodes, the present invention provides a rapid, reliable, portable and inexpensive means of detecting low lead levels. The colloidal gold modified electrodes have microelectrode array characteristics and produce significantly higher stripping detection signals for lead than are produced at bulk gold electrode surfaces. The method is effective in determining levels of lead down to at least 5 μg/dL in blood samples as small as 10 μL.

22 Claims, 9 Drawing Sheets

OTHER PUBLICATIONS

Guilbault et al., "Homovanillic Acid as a Fluorometric Substrate for Oxidative Enzymes," *Analytical Chemistry*, 40(1):190–196, 1968, no month available.

Guilbault, "Determination of Inhibitors," *Enzymatic Methods of Analysis*, Pergamon Press, pp. 197–209, 1970, published in Great Britain, no month available.

Holleck, "The Reduction of Chlorine on Carbon in $AlCl_3$–KCl, NaCl Melts," *Journal of the Electrochemical Society*, 119(9):1158–1161, no month and year available.

"U.S. CDC Releases Revised Guidelines on Childhood Lead Poisoning—Blood Lead Level of Concern Lowered to ≳10 µg/dl," *ILZRO Enviornmental Update*, 1(10):2, 1991, no month available.

Kamata & Onoyama, "Lead–Selective Membrane Electrode Using Methylene Bis (diisobutyldithiocarbamate) Neutral Carrier," *Analytical Chemistry*, 63:1295–1298, 1991, no month available.

Kratochvil et al., "Effect of Metals on the Activation and Inhibition of Isocitric Dehydrogenase," *Analytical Chemistry*, 39(1):45–51, 1967, no month available.

Linde, "Estimation of Small Amounts of Fluoride in Body Fluids," *Analytical Chemistry*, 31(12):2092–2094, 1959, no month available.

Morrissey & Han, "The Conformation of γ–Globulin Adsorbed on Polystyrene Latices Determined by Quasielastic Light Scattering," *Journal of Colloid and Interface Science*, 65(3):423–431, 1978, no month available.

Sheikh & Townshend, "Applications of Enzyme–Catalysed Reactions in Trace Analyses—VII," *Talanta*, 21:401–409, 1974, published in Great Britain, no month available.

Smit & Cass, "Cyanide Detection Using a Substrate–Regenerating, Peroxidase–Based Biosensor," *Analytical Chemistry*, 62:2429–2436, 1990, no month available.

Toren & Burger, "Trace Determination of Metal Ion Inhibitors of the Glucose–Glucose Oxidase System," *Mikrochimica Acta (Wien)*, pp. 538–545, 1968, no month available.

Tran–Minh et al., "Studies on Acetylcholine Sensor and its Analytical Application based on the Inhibition of Cholinesterase," *Biosensors & Bioelectronics*, 5:461–471, 1990, no month available.

Smith, "Air Pollution and Forest Damage," *Chemical and Engineering News*, pp. 30–42, Nov. 11, 1991.

Trade Brochure: esa, Inc. Trace Metal Analyzer Brochure, Bedford, Mass, 1990, no month available.

Gunasingham et al., "Performance and Evaluation of a Handheld Electrochemical Monitor for Toxic Metals," Cole–Parmer Instrument Company, Chicago, Illinois, no month and year available.

Crumbliss, A. L., Henkens, R. W., Kitchell, B. S., Perine, S. C. Stonehuerner, J., and Tubergen, K. R., "Amperometric Glucose Sensor Fabricated from Glucose Oxidase and a Mediator Co–Immobilized on a Colloidal Gold Hydrogel Electrode," *Biosensors Technology: Fundamentals and Application*, Chapter 13, 1990, published in USA, no month available.

Crumbliss, A. L., Henkens, R. W., Hunter, K., Kitchell, B. S., O'Daly, J. P., Stonehuerner, J., and Tubergen, K. R., "The Influence of Colloidal Gold Surfaces on Enzyme Activity," ACS North Carolina Divisional Meeting, Sep. 1988, published in USA.

Crumbliss, A. L., Henkens, R. W., Kitchell, B. S., Perine, S. C., Stonehuerner, J., and Tubergen, K. R., "Amperometric Glucose Sensor Fabricated from Glucose Oxidase and a Mediator Co–Immobilized on a Colloidal Gold Hydrogel Electrode," ACS North Carolina Divisional Meeting, University of North Carolina at Chapel Hill, Sep. 7–9, 1989, published in USA.

Crumbliss, A. L., Kitchell, B. S., Perine, S. C., Stonehuerner, J., Tubergen, K. R., Zhao, J., and Henkens, R. W., "Catalytic and Electroactivity of Irreversibly Adsorbed Enzymes at Gold Electrode Surfaces," Symposium on Protein Electrochemistry: ACS Southeast Regional Meeting (SERM), Oct., 1989, published in USA.

Crumbliss, A. L., Henkens, R. W., Kitchell, B. S., McLachlan, K. L., O'Daly, J. P., Perine, S. C., Stonehuerner, J., Tubergen, K. R., and Zhao, J., "The Use of Inorganic Materials to Control or Maintain Immobilized Enzyme Activity," Symposium on opportunities for inorganic chemistry in biotechnology, ACS National Meeting in Boston, Apr. 23, 1990, published in USA.

Henkens, R. W., Kitchell, B. S., O'Daly, J. P., Perine, S. C., and Crumbliss, A. L., "Bioactive Electrodes Using Metallo Proteins Attached to Colloidal Gold," *Recl.: Trav. Chim. Pays Bas*, 106:298, 1987, no month available.

Henkens, R. W., Zhao, J., and O'Daly, J. P., "Multi–Analyte Enzyme Electrodes for Environmental Monitoring," Proceedings of *5th International Biotechnology Conference in Copenhagen*, Jul. 8–13, 1990.

Sakai et al., "Determination of Heavy Metal Ions by Urea Sensor Using ISFET," *Sensors and Materials*, 2(4):217–227, 1991, no month available.

Sheikh, R. A., "The Determination of Nanogram Amounts of Indium, Lead and Drugs of Forensic Importance by Enzymic Inhibition," Proc. Soc. Analyt. Chem., 10(11):263–286, 1973, no month available.

PCT Search Report mailed Apr. 5, 1993.

Lord Jr., S. S. et al., "Coulometric Determination of Submicrogram Amounts of Wilver," *Anal. Chem.*, 24:209–213, 1952, no month available.

Moeremans, M. et al., "Sensitive Colloidal Metal (Gold or Silver) Staining of Protein Blots on Nitrocellulose Membranes," *Anal. Biochem.*, 145:315–321, 1985, no month available.

Wang, J. and Tian, B., "Mercury–Free Disposable Lead Sensors Based on Potentiometric Stripping Analysis at Gold–Coated Screen–Printed Electrodes," *Anal. Chem.*, 65:1529–1532, 1993, no month available.

Wojciechowski, M., Balcerzak, J., "Square–Wave Anodic Stripping Voltammetry at Glassy–Carbon–Based Thin Mercury Film Electrodes in Solutions Containing Dissolved Oxygen," *Anal. Chem.* 62:1325–1331, 1990, no month available.

COLLOIDAL-GOLD ELECTROSENSOR MEASURING DEVICE the government may own certain rights in the present invention pursuant to Small Business Innovative Research grant number DE-FG05-94ER81657 from the U.S. Department of Energy.

The present application is a continuation-in-part of U.S. patent application Ser. No. 08/073,806, filed Jun. 7, 1993, now U.S. Pat. No. 5,368,707; which is a continuation-in-part of U.S. patent application Ser. No. 07/821,732, filed Jan. 15, 1992, now issued as U.S. Pat. No. 5,217,594 on Jun. 8, 1993. The entire text of each of the above-referenced disclosures is specifically incorporated by reference herein without disclaimer.

BACKGROUND OF THE INVENTION

1. Field of the Invention

The invention relates generally to the field of electrochemical sensor technology and specifically to sensors that utilize colloidal gold to detect metals and to methods of using the sensors for small volume determination of submicromolar levels of these analytes.

2. Description of the Related Art

Lead is a toxic heavy metal that affects all body systems and is ubiquitous in industrialized society. Children are especially at risk. It is estimated that in the United States 3 million out of a total population of 24 million children under the age of six have lead poisoning. It is reported that blood lead as low as 10 µg/dL is responsible for adverse effects on intelligence and behavior with negative endocrinological and hematological impacts. The U.S. Centers for Disease Control (CDC) has set the blood lead action level at 10 µg/dL for children under six and recommends that this population be screen-tested annually. There is a need for new, portable, low-cost, technology to meet this goal.

CDC's identification of the magnitude of this problem has created a demand for a portable instrument capable of detecting low blood-lead and low environmental-lead levels. A simple to use easily transported lead measuring device would be particularly useful in remote locations where clinics and doctors offices are not accessible to the population and where highly trained technical personnel are not available.

Increasingly, undesirable chemicals are released into the environment as a result of manufacturing processes and waste disposal activity. Unfortunately, these substances leach into soil, into water supplies, and eventually into the food chain. The ideal solution is to prevent pollution at the source; even so, a first consideration is to determine whether or not an undesirable compound is present in a specific location.

The measurement of lead in solution by stripping analysis is a well-established technique. Traditionally, this technique has relied on laboratory based instrumentation, skilled operators, reusable electrodes, and the use of mercury metal. The most popular currently used technique for blood-lead measurement is anodic stripping voltammetry (ASV) utilizing reusable large area graphite-mercury composite electrodes. However, this technology is complicated, expensive for routine use, and relatively insensitive. Additionally, the use of mercury has several drawbacks, including volatility and toxicity. Mercury in any form is toxic. Its effects are particularly insidious because toxicity is cumulative, building up after successive exposures to even relatively small amounts of the metal. Because mercury is a liquid, it requires special precautions and considerations in handling.

The testing procedures presently available are not suitable to meet the public demand for mass blood-lead screening. Because ASV utilizes reusable electrodes, the technique requires a well-trained and experienced analytical chemist to conduct a reliable electrochemical measurement. This is because the electrode must be restored and prepared for each analytical session.

There is therefore a need to develop rapid, simple and reliable tests for determining trace amounts of different classes of materials, especially molecular entities such as trace elements and contaminants. Furthermore, a means of simple, reliable and rapid on-site testing is needed to detect such molecules in remote or non-institutional locations in the field, in small clinics, doctors' offices, or even in the home. A particularly useful application includes testing body-fluid samples and environmental samples for trace elements by relatively unskilled personnel.

Likewise, a simple, rapid, disposable, and inexpensive analyte detection system would greatly benefit developing countries that may lack access to the sophisticated equipment, facilities and trained personnel necessary for traditional testing methods. Finally, methods are needed to detect trace levels of analytes, so that effective, point source detection of environmental pollutants and areas of contamination can be more easily identified.

Traditional stripping voltammetry is performed primarily with mercury or mercury modified electrodes because mercury affords easy surface regeneration and formation of alloys to prevent surface change or fouling. However, mercury is toxic and mercury or mercury modified electrodes are not stable for repeated or continuous monitoring.

Certain gold surfaces do form alloys with metals, although the capacity may not be as great as mercury film. However, a gold film is much more stable than a mercury film electrode and the formed gold alloy can be restored to the original gold film electrode electrochemically after the stripping. This indicates the feasibility of using gold based electrodes for continuous monitoring of some heavy metals through selected amperometric processes.

Coulometry and other electrochemical techniques have been applied to the analysis of metals at polycrystalline solid electrodes (Lord et al., 1952; Nicholson, 1957; Nicholson, 1960; Hamelin, 1979; Wang and Tian, 1993; Wojciechowski and Balcerzak, 1990). Quantitation of deposition and dissolution of metals (stripping analysis) on solid electrodes such as Pt or Au has advantages in the possibility to analyze metals more electropositive than mercury, and in greater sensitivity because deposited metal is recovered more completely (Nicholson, 1957).

While platinum (Pt) has been employed for stripping analysis of the greatest number of metals (Lord et al., 1952; Nicholson, 1957; Nicholson, 1960), gold (Au) has been employed for trace analysis of lead in aqueous solution (Wang and Tian, 1993; Wang, 1985; Copeland and Skogerboe, 1974; Posey and Andrew, 1980). Lead in dilute acid solution has been detected and results shown analytically useful in deposition at Au films (Wang and Tian, 1993) and Pt wires (Lord et al., 1952). On Au films plated on carbon substrates, lead has been detected to 2.5 ppb (12.5 nM) (Wang and Tian, 1993). Similar results for analysis of nickel (Ni) at Pt and Au have been shown,.suggesting that extension of analysis from one noble metal to another as a stripping substrate is reasonable (Nicholson, 1957).

Hydrogen evolution on gold in aqueous solution is suppressed by deposition of even submonolayer coverages of lead (Hamelin, 1979), but dissolved oxygen may interfere in voltammetric analysis of trace metal levels-in stripping at Au or Pt (Nicholson, 1960). While lead on Au at submonolayer coverages shows no alloy formation (Hamelin, 1979), higher coverages (bulk deposits) may yield alloys (Biberian and Rhead, 1973; Perdereau et al., 1974).

Deposition of lead occurs on Pt or Au in the range of potentials −0.55 V to −0.7 V (vs. S.C.E.). Solution conditions range from pH 2 (0.01M HClO4) to pH −5 (0.1M KCl). Depositions have been employed in stirred or unstirred solution, for times ranging from 0.5 to 10 minutes (or greater for unstirred solutions of trace levels of metal). Scans through the dissolution potential range yield peaks with FWHM<100 mV (on Pt) (Lord et al., 1952) and Au (Wang and Tian, 1993). Cleaning of the surface, when necessary, has been accomplished by formation and reduction of Au oxide (Hamelin, 1979).

Monodisperse colloidal gold particles having diameters ranging from 50 to 1,000 Å have a large surface area per unit volume and have found extensive use as markers in electron microscopy (Housberger, 1981). Colloidal gold particles have been labeled by the adsorption of a variety of biological macromolecules, including toxins, antibodies, proteins, and enzymes (BBI International). Gold is also an excellent electrode material with good heterogeneous electron transfer characteristics (Sawyer and Roberts, Jr., 1974).

SUMMARY OF THE INVENTION

The present invention addresses the foregoing and other problems in the prior art. In particular, novel electrodes are provided for the electrochemical determination of low concentrations of metal ions. The inventors have developed electrodes that now for the first time make available a convenient, rapid, and inexpensive method of determining blood lead levels. The working electrode surface is modified with colloidal gold particles, thereby providing several advantages over other conventional conducting materials, including bulk gold. The disclosed electrodes are conveniently set up for use with square wave coulometric determination of metal ion levels.

Colloidal gold sols and particles have particular advantages for the disclosed invention. The use of non-toxic colloidal gold replaces the toxic, volatile, liquid mercury traditionally used in stripping analysis. Colloidal gold particle size and sol concentration are manipulable through synthetic technique. Colloidal gold sols are easily deposited through well-developed liquid handling techniques. The electrochemical activity relative to mass is greater than for bulk gold. The lead sensitivity of colloidal gold modified carbon electrodes is greater than the lead sensitivity of bulk gold electrodes.

Square wave coulometry (SWC) is a novel electroanalytical method that combines fast scanning square wave voltammetry with coulometric measurement of the signal. The version of SWC which is used in this invention employs square wave voltammetry for anodic stripping of metals such as lead on gold electrodes. The net charge consumed for anodic stripping during the square wave voltammetric scan constitutes the coulometric stripping signal. Square wave voltammetry offers many advantages for anodic stripping analysis over more popular stripping techniques such as differential pulse voltammetry. Advantages include enhanced sensitivity, shorter analysis time and more effective discrimination against background currents. Coulometric stripping signals also offer additional advantages over traditional stripping peak current based signals. Coulometric signals experience reduced interference from variations in the kinetics of the stripping process caused by non-metallic sample components, intermetallic interactions between the analyte metal and other metals, and intermetallic interactions between the analyte metal and the electrode metal. In addition, coulometric stripping signals offer better discrimination against electronic noise, a feature that is particularly beneficial for measurements involving microelectrode arrays. A particular advantage for a rugged, simple, portable device (such as the lead sensor of the present invention) is that SWC lead analysis does not require removal of dissolved oxygen from the sample solution as is required for other stripping techniques.

Although square wave voltammetry with SWC analysis has advantages of sensitivity and speed, other voltammetric techniques well-known to those skilled in the art, may be used with the disclosed colloidal gold modified carbon electrodes to measure lead. Some of these techniques include linear scan voltammetry, staircase voltammetry, and differential pulse voltammetry.

The present invention, in a preferred embodiment, concerns the use of an electrochemical stripping sensor that employs SWC measurement of blood-lead. In particular, conducting inks are screen printed on a supporting material to fabricate reference, counter and working electrodes. Colloidal gold sol mixed with poly(ester-sulfonic acid) is preferred for providing better sensitivity to lead in sample solution. Controlled deposition of colloidal gold sol mixed with poly(ester-sulfonic acid) polymer onto the surface of the working electrodes by techniques such as ink-jet printing, volumetric deposition, and air brush spraying provides better reproducibility and eliminates waste of reagents due to the non-contact nature of these processes.

Colloidal gold surfaces deposited on the working electrodes have significant advantages over the mercury surfaces conventionally employed. The gold is nontoxic, nonvolatile, and is employed as a solid rather than a liquid. Gold is relatively inert. Colloidal gold, by comparison with bulk gold, requires less material deposited on the electrode surface in order to perform a function similar to that of a gold film. The use of colloidal gold rather than bulk gold therefore results in a less expensive product. This is attractive from a commercial standpoint.

The lead signal response per active area of colloidal gold is greater than the lead signal response per active area of bulk gold. The lead signal response per mass of colloidal gold is much greater than the lead signal response per mass of bulk gold. This is attractive from a performance standpoint.

By way of explanation but in no way indicating a limitation to the invention, it is believed that a colloidal gold modified carbon surface acts as a microelectrode array. This is evidenced by the inventors' observation that the lead signal charge density in very small volume samples, without stirring during analysis, for colloidal gold modified carbon electrodes is about 100 times greater than the lead signal charge density in very small volume samples, without stirring during analysis, for bulk gold electrodes. This appears to contribute to the advantages of colloidal gold modified carbon electrodes over bulk gold electrodes.

A further advantage of a colloidal gold modified carbon electrode acting as a microelectrode array is increased efficiency of mass transport of lead ions to the microelectrode surface during deposition. This allows deposition of sufficient amounts of lead for subsequent stripping in a relatively short period of time (90 seconds) without forced convection (stirring or other forms of mass transport enhancement). The amount of lead deposited on the colloidal gold modified carbon electrode under these conditions is sufficient to generate stripping currents in the nanoampere (nA) range. Currents in this range can be measured with simple, unsophisticated, and inexpensive potentiostatic systems.

The present invention uses improved stripping technology and colloidal-gold modified electrodes to replace expensive, unstable, and toxic mercury based ASV electrodes with inexpensive, disposable, and colloidal-gold based SWC electrodes. Colloidal gold is a special form of this benign and versatile metal in which the material is not in a bulk solid (like an expensive platinum electrode) or in a volatile and vulnerable liquid (like toxic mercury) but in discrete spheroid particles. The amount of gold particles used is on the nanogram scale thereby lowering the material cost per electrode.

The novel electrodes of the present invention are formed by the controlled deposition of nanometer-sized colloidal-gold particles onto carbon electrodes. Controlled deposition is possible because colloidal gold sols are readily compatible with well-developed liquid handling techniques such as ink-jet printing, volumetric deposition, and air brush spraying. Devices used in these techniques are capable of measuring a quantitative volume of a liquid like colloidal gold sol and applying it to prescribed areas on a surface. Size of the gold particles may range from 100–700 Å; however, for most purposes the inventors have found that particles in the range of 200–500 Å are preferred.

The carbon electrodes may be glassy carbon or fabricated by screen-printing carbon ink onto the surface of an insulating material. Application of the colloidal gold particles to the carbon electrode is quantitative and precisely directed by state-of-the art deposition techniques. The result is a carbon electrode studded with an array of nanometer-sized gold particles. Carbon electrodes exhibit several orders of magnitude less sensitivity for lead detection by SWC analysis than colloidal gold modified carbon electrodes. The disclosed colloidal gold modified carbon electrode design is able to reliably measure 5 μg lead/dL blood in approximately 2 minutes. The detection limit for blood lead, defined as 3 times the standard deviation of the baseline, is 0.3 μg/dL.

Numerous embodiments of the disclosed electrodes are envisioned, including disposable electrodes. The disposable electrode may be inserted into a hand-held electronic meter that is pre-programmed with a square wave coulometric (SWC) electrochemical measurement technique. The blood-lead test operator takes a 10–100 μL blood sample, adds a simple acid treatment agent, and places the treated sample on the electrode. The operator then pushes one button and the electronic meter executes the entire SWC analysis in approximately 2 minutes. When the analysis is completed the result is displayed by an LCD screen in μg/dL (or any desired units). The data may be stored in memory contained in the electronic meter and can be uploaded to a personal computer or network for further manipulation. Information storage, retrieval, and transfer capabilities may also be used for epidemiological data collection and analysis.

The invention includes methods of detecting blood lead levels by taking advantage of the characteristics of the disclosed colloidal gold electrodes. In a particular embodiment, blood lead levels may be accurately, rapidly and inexpensively determined to levels as low as 5 μg/dL. The inventors have discovered that the problems inherent in blood lead measurements can be overcome by treating the lead with an acid prior to determining lead using stripping methods. Generally one will wish to employ a mineral acid e.g., HCl, $HNO_3$, and the like, to adjust the pH of the sample to below pH 1. The acid effects complete and rapid chemolysis of red blood cells, resulting in release of intracellular lead. The use of a low pH assures that lead is completely released, even when bound to EDTA, an anticoagulant frequently employed when blood samples are drawn.

While other acid treatment reagents may be employed, the inventors have found that the procedures described with HCl, and in particular with solutions of 400 mM HCl have provided the following advantages:

a) Fragmentation of cell membranes is extensive and precipitated cell debris remain in a colloidal form for hours after the treatment.

b) Blood proteins precipitate quickly in a form of colloidal suspension.

c) Precipitated proteins, cell debris and other blood components do not undergo extensive coagulation. This results in retention of the liquid properties of blood sample after treatment.

d) Extensive polymerization of proteins and other blood components, which is often the case when other acid-treatment reagents are used, does not occur long after the treatment. As a result, the sample retains its liquid character for several hours after the treatment. Also the viscosity of the treated sample does not change significantly over relatively long periods of time which would affect the measured stripping signal for lead.

e) There are no electroactive components in the treated blood that interfere with the stripping methods used to determine lead levels.

The disclosed methods may be used for square wave coulometric determination of lead in untreated blood, EDTA treated blood, and heparin treated blood samples. The blood may be unlysed, partially lysed or completely lysed prior to treatment. Samples may be fresh, refrigerated or frozen and thawed. The method has been shown to work with human and bovine blood and is expected to be applicable to all mammalian blood.

The disclosed methods may be used also for square wave coulometric determination of lead in urine, water, and various other aqueous samples. The sensitivity of the disclosed methods for detecting lead in water samples is 10 times greater than for detecting lead in blood samples. The inventors have reliably measured 0.1 μg lead/dL water in approximately 2 minutes using the disclosed system. The detection limit for water lead is 0.02 μg/dL.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
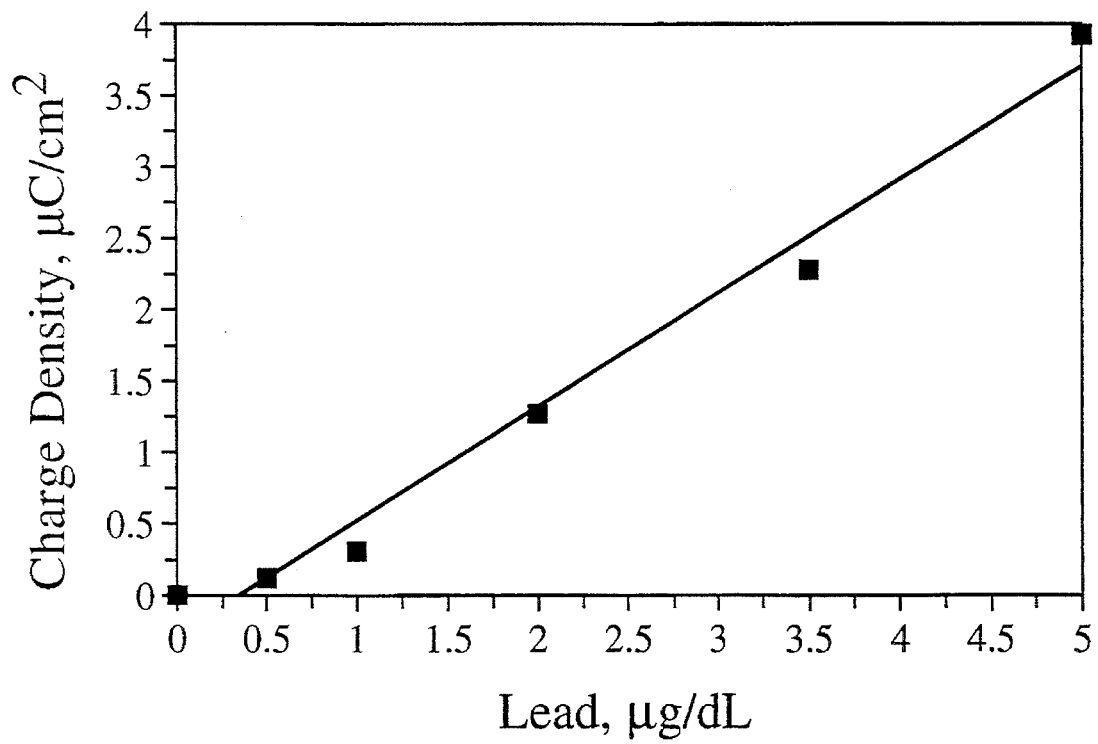
FIG. 1 is a graph showing the increasing charge density, measured in microcoulometers per square centimeter, with increasing lead ion concentration in water determined with a colloidal gold modified carbon electrode. Lead concentrations are the lead concentrations at the time of analysis.

The present invention is an electrochemical stripping sensor that employs colloidal gold modified electrode detection and square wave coulometric (SWC) measurement of lead in blood, urine, water and other sample materials. The use of colloidal gold modified electrodes has been previously described in U.S. Pat. No. 5,217,594.

The lead detection system of the present invention provides an easy-to-use, accurate and portable test system to detect lead levels in human blood, other body fluids, and environmental samples such as ground and surface waters. The fundamental technology of the square wave coulometric (SWC) lead test involves specific electrochemical deposition of sample lead onto a colloidal gold modified carbon electrode, stripping the deposited lead, and coulometric analysis of the measured lead stripping current. The area-function that represents the lead stripping current is proportional to lead concentration and can be equated to lead in blood and other samples in µg/dL.

The analytical challenge for a practical device to screen all children under the age of six for blood lead is met in a portable device by employing the colloidal gold modified sensor strip of the present invention. The system achieves accurate and precise results at current CDC guidelines for lead of 10 µg/dL and below. The present invention, in addition to being accurate, precise, portable and cost-effective, is relatively simple and easy-to-use so that individuals without extensive training obtain acceptable results in "real world" situations.

The colloidal gold modified electrodes of the present invention require only a simple acid pre-treatment step for a blood sample prior to electrochemical analysis. It is possible for a relatively nontechnical personnel to handle a large number of samples in a relatively short period of time, thereby saving time and money.

The system includes a reusable electronic meter and a square wave coulometric analysis protocol. The reusable electronic meter is a light-weight (~1 lb), durable, internally or externally powered electrochemical instrument. One selects a meter to display test results on an LCD screen and/or store data in internal memory. A convenient meter feature is an RS-232 port so that stored data can be downloaded to a personal computer or network for further analysis or long-term storage. Existing epidemiological information may also be stored in the meter's internal memory for remote access and acquired data for epidemiological analysis can be downloaded for expanding shared databases. The square wave coulometric analysis protocol is programmed into the microprocessor contained in the reusable electronic meter. The dimensions of the meter are not critical and may be of a convenient size for lap-top or hand-held use.

The disposable sensor strip configuration of the present invention is a small (~1 inch), rugged, printed, colloidal gold modified carbon stripping electrode. The foundation for the sensor strip is an inert polymer material. One first selects a large polymer sheet suitable for screen printing. This sheet may be screen printed with any array of carbon and silver 3-electrode groupings. A dielectric material is next applied to protect the electrodes and form a recessed sample application area. Colloidal gold is applied by controlled deposition techniques to the lead-sensing working electrode. The polymer sheet is then cut into discrete sensor strips, each sensor strip containing one 3-electrode grouping, and packaged.

The disposable colloidal gold modified sensor strip fits into a port on the reusable electronic meter in a manner to make electrical contact with the meter, and to keep the sample application area away from the meter to prevent contamination. Acid treated sample (e.g., blood or other sample) is applied to the sensing (colloidal gold modified) area of the electrode. The operator then pushes a button on the electronic meter and the SWC analysis proceeds to completion in ~2 minutes. The concentration of blood lead is displayed on the meter's LCD. The blood contaminated sensor strip is removed from the meter and discarded in a safe manner.

The following examples are included to demonstrate preferred embodiments of the invention. It should be appreciated by those of skill in the art that the techniques disclosed in the following examples represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The colloidal gold modified electrodes of the present invention are prepared by controlled deposition of a colloidal gold solution onto a suitable substrate, such as glassy carbon or printed carbon ink. In certain modifications, the inventors have achieved excellent reproducibility by stabilizing colloidal gold sol solutions with a cationic polymer. The polymer apparently acts a dispersant as well as a stabilizer of the gold sol. An unexpected advantage of adding a polymer stabilizer is the elimination of background interference, possibly by selective membrane retention of interfering electrochemical species by the polymer. Without the polymer, problems with interfering electrochemical species were frequently encountered. Polymer addition may also lower the background current by blocking some of the conducting surface sites. Typical preparations of a colloidal gold sensor electrode are described in this example.

The disposable sensor strip is comprised of a three-electrode system. Each electrode has a different function. The silver electrode provides an electrochemical reference during the measurement. The carbon electrode provides a counter pole for the working electrode. The colloidal gold modified carbon electrode is the working electrode and provides the lead deposition and stripping surfaces. These electrodes are prepared by screen printing three electrodes with conductive silver ink and then screen printing carbon ink over the counter and working electrode. The carbon working electrode is completed by the controlled volumetric deposition and evaporation of a known volume of colloidal gold sol/poly(ester-sulfonic acid) polymer mixture on the electrode surface.

Colloidal Gold Solutions

Gold trichloride (Fisher Chemical Company, St. Louis, Mo.) was used to prepare a colloidal gold sol with a particle diameter of approximately 300 Å by the method of Moremans, et al, (1985). A solution of 1% aqueous sodium citrate was added to a rapidly boiling, stirred solution of gold trichloride, and the solution was refluxed for 30 minutes. The final concentrations (weight percent) were 0.01% $HAuCl_4$ and 0.03% sodium citrate.

Gold trichloride (Fisher Chemical Company, St. Louis, Mo.) was reduced with ascorbic acid to prepare a colloidal gold sol with a particle diameter of approximately 500 Å. The reaction was carried out at 0° C. and accomplished by the addition of ascorbic acid to a dilute solution of $HAuCl_4$ (ratio 5 moles ascorbic acid per mole of $HAuCl_4$). The reaction solution is stirred for 90 minutes at 0° C. During the course of the reaction there was a gradual color shift from deep purple to red wine color indicating a maturation in particle size distribution. Final size distribution of the colloidal gold did not occur for a least another 4 hours at room temperature. This method produced a colloidal gold suspension substantially equivalent to the citric acid reduction without using elevated temperatures.

Colloidal gold sols with particle diameters ranging from 100 Å to 1000 Å were purchased from BBI International, UK.

Gold electrode preparation

Dilute colloidal gold (0.05 mg/ml) was concentrated 20 times by centrifugation for 30 minutes at 4000 rpm. Poly(ester-sulfonic acid) polymer (Eastman Chemical, Kingsport, Tenn.) was added to a final concentration of 0.9% (v/v). Three microliters of the (1 /mL) colloidal gold sol/poly(ester-sulfonic acid) polymer solution was volumetrically deposited on the working electrode surface and spread to cover the entire exposed surface of the working electrode. The electrode was then dried at 30°–40° C. under a heat gun for 5 minutes. In this example, the working electrode surface was modified with 3 µg of gold.

As an alternate to the above preparation, three microliters concentrated colloidal gold sol (1 mg/mL) was volumetrically deposited on the working electrode surface and spread to cover the entire exposed surface of the working electrode. The electrode was then dried at 30°–40° C. under a heat gun for 5 minutes. Two microliters of 2% (v/v) poly(ester-sulfonic acid) polymer was volumetrically deposited onto the colloidal gold modified working electrode surface and dried for another 5 minutes.

EXAMPLE 2

SWC Stripping Determination of lead in Water

Six water samples were tested. The samples were doped with lead to concentrations of 0 µg/dL, 0.5 µg/dL, 1.0 µg/dL, 2.0 µg/dL, 3.5 µg/dL, and 5.0 µg/dL respectively. The doped lead values were confirmed by anodic stripping voltammetry.

Carbon working electrodes were modified with 3 µL of 1 mg/mL 500 Å colloidal particles or with 3 µL of 1 mg/mL 500 Å colloidal particles with 1% poly(ester-sulfonic acid) polymer as described in Example 1. Water samples were pretreated with 100 mM HCl solutions. Water (30–50 µL) was placed on the disposable 3-electrode sensor strip, described in Example 1, so as to cover all three electrodes within the circle of the insulating layer. A square wave coulometry (SWC) program was initiated within 10 seconds of application of the sample on the disposable sensor strip. Execution of the measurement sequence was confirmed by the monitor reading "Test in Progress". Within approximately 2 min. the display showed a lead concentration value. Results for colloidal gold modified carbon electrodes are shown graphically in FIG. 1. Results for colloidal gold particles with 1% poly(ester-sulfonic acid) polymer modified carbon electrodes are shown graphically in FIG. 2.

Figure 3:
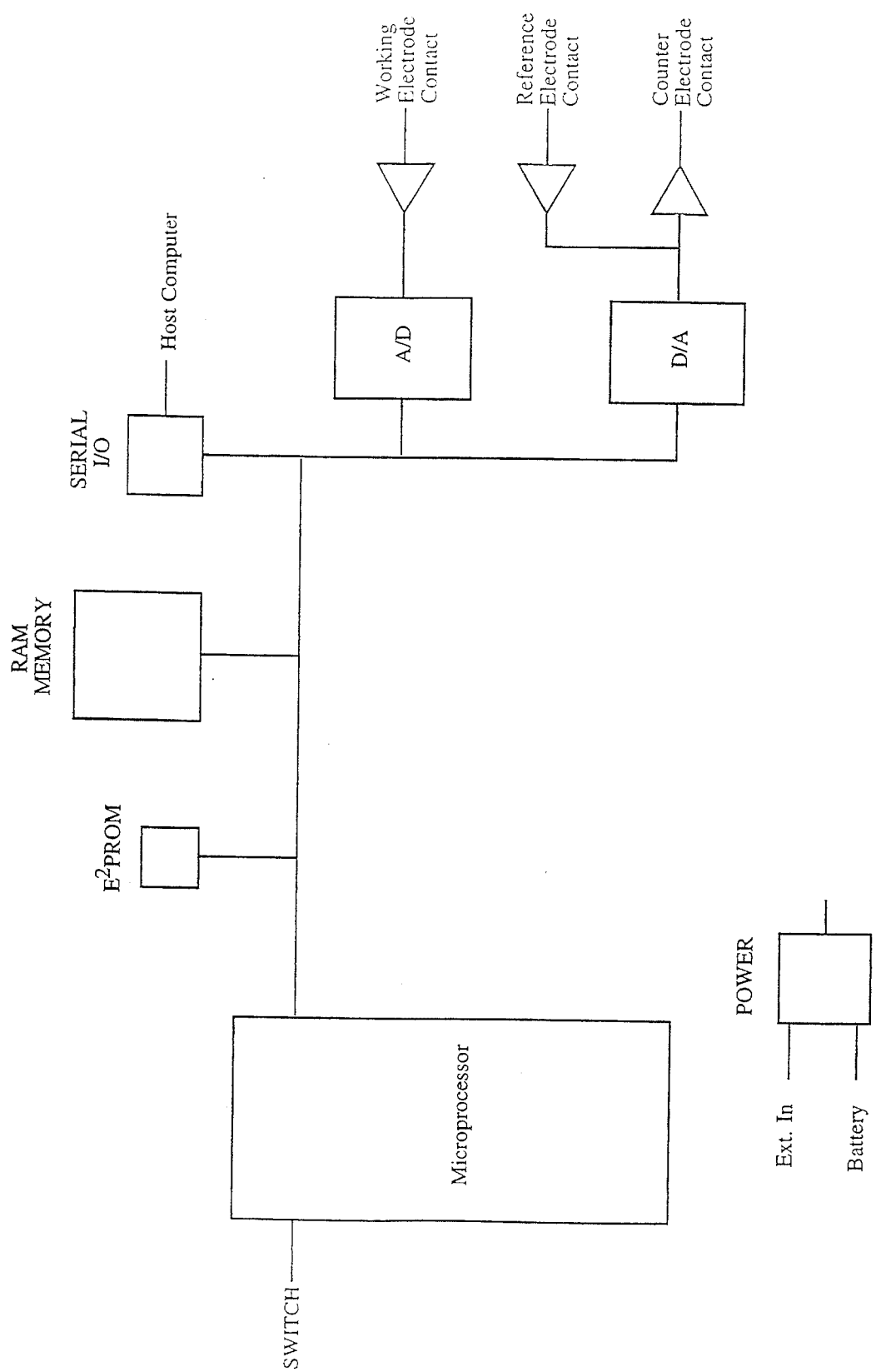
FIG. 3 is a block diagram of the reusable electronic meter's components.

The colloidal gold modified carbon electrodes were coupled to a reusable electronic meter that provided the potentiostatic and SWC analytical capabilities for the disclosed lead detection system. The meter can vary in size from hand-held to lap-top to table top dimensions. A block diagram of the reusable electronic meter's components is shown in FIG. 3.

The reusable electronic meter's microprocessor automatically executes the following sequence:

Conditioning 1: A potential of −500 mV (vs. the silver reference electrode on the disposable sensor strip) is applied to the strip's working electrode (colloidal gold modified carbon) for 10 seconds.

Conditioning 2: The potential is changed to −50 mV and held at this value for 10 seconds.

Deposition: The potential is changed back to −500 mV and held for 90 seconds.

Stripping and data acquisition: A square wave voltammetry scan is run from −500 mV to +50 mV, during which currents are measured (twice during each square wave cycle) and saved in the memory of the meter (552 measurements per scan). The parameters of this square wave voltammetry are: frequency 50 Hz, amplitude 25 mV, potential step 2 mV.

Data treatment: Stored current values are numerically filtered (forward and reverse and net currents are filtered individually). A baseline subtraction algorithm is then executed and the lead stripping signal is measured by another algorithm that integrates the area under the stripping peak. The peak area value is then correlated with standard calibration data to determine the concentration of lead in the analyzed blood sample.

EXAMPLE 3

The advantages of colloidal gold modified carbon electrodes compared with thin film (bulk) gold electrodes are not necessarily predicted or expected. The inventors have tested both types of electrodes in order to compare properties. The following describes direct comparisons of stripping voltammetry determinations of lead ion between colloidal gold modified carbon electrodes and bulk gold electrodes in the same samples and under the same experimental and instrumental conditions.

In order to compare the sensitivity of a conventional, reusable, solid gold ("bulk gold") disk electrode with the disclosed colloidal gold modified carbon electrode (prepared with 1.0 mg/mL 500 Å colloidal gold sol and 1.0 mg/mL 500 Å colloidal gold sol mixed with 1% poly(ester-sulfonic acid) polymer), a series of parallel SWC measurements of lead stripping response was conducted in 100 mM HCl solutions containing 0–5 mg/dL (equivalent to 0–50 ppb) of lead standard. Such comparison can be meaningful only if the sensitivity is related to the active surface area of the compared electrodes. This can be done by either considering the geometric surface areas of the electrodes or considering the active surface areas of the electrodes. The former introduces an uncertainty related to the roughness of the electrode surface and the fact that the colloidal gold particles not in contact with the carbon support do not participate in the stripping process. The comparison of the sensitivity per active surface area is free of these uncertainties and therefore more meaningful.

The bulk gold electrode had a diameter of 1.8 mm and a geometric surface area of 1.5 mm$^2$. The screen printed carbon ink electrode had a geometric surface area of 14.6 mm$^2$. The geometric surface area of the colloidal gold particles deposited on this carbon electrode was 18.7 mm$^2$. The colloidal gold geometric surface area calculation was based on the number of colloidal gold particles (determined from the measured average particle size), colloidal gold concentration, assuming ideal sphericity of gold particles, and ignoring the roughness of the gold particle surface.

The active electrode surface area was determined by measuring the charge required to reduce anodically oxidized gold from the electrode surface. This is a commonly accepted method of surface area determination for platinum and gold electrodes. A series of cyclic voltammetry (CV) experiments was conducted using each gold electrode and the same reference (silver ink on the sensor strip) and counter (carbon ink on the sensor strip) electrodes. Solutions (with ambient dissolved oxygen) of 100 mM HCl were used. The charge was measured by integration of a noise-filtered and background- and baseline-subtracted reduction peak for $Au^{+1}$ species generated during the 100 mV/s CV scan from 0.0 V to 1.2 V to −0.5 V (vs. Ag reference electrode). The measurements were repeated to assure reproducibility. The measured charge was then divided by 3.86 mC/mm$^2$, which is the literature value of the standard charge per unit surface area for electrooxidation of gold. The surface area values obtained were 52.6 mm$^2$ for the bulk gold electrode and 2.6 mm$^2$ for the colloidal gold modified carbon electrodes.

Figure 2:
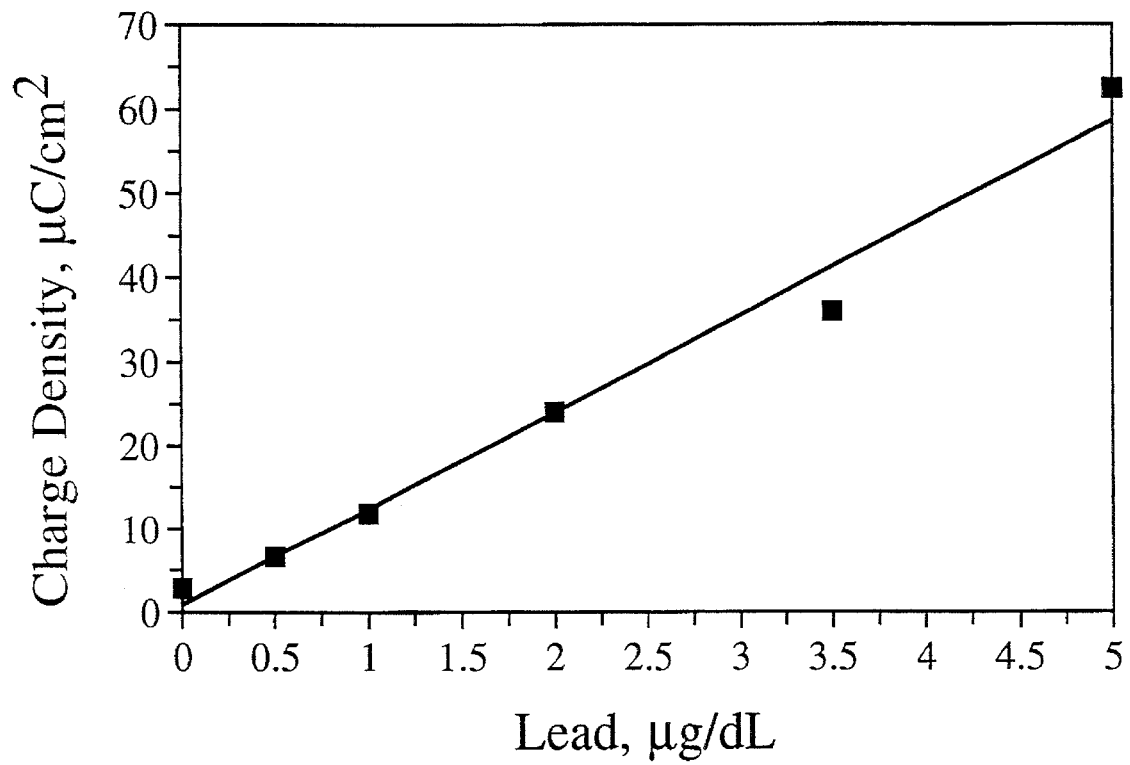
FIG. 2 is a graph showing the increasing charge density, measured in microcoulometers per square centimeter, with increasing lead ion concentration in water determined with a colloidal gold mixed with poly(ester-sulfonic acid) polymer modified carbon electrode. Lead concentrations are the lead concentrations at the time of analysis.
Figure 4:
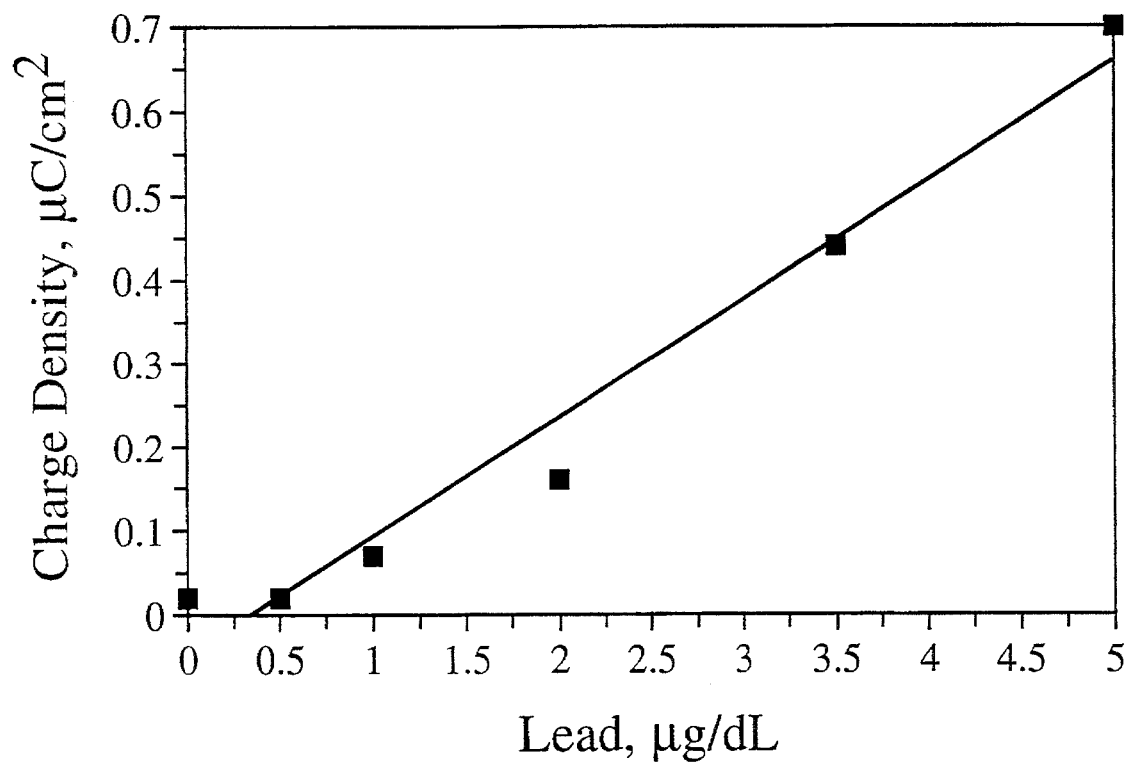
FIG. 4 is a graph showing the increasing charge density, measured in microcoulometers per square centimeter, with increasing lead ion concentration in water determined with a bulk gold electrode. Lead concentrations are the lead concentrations at the time of analysis.

FIG. 4, FIG. 1, and FIG. 2 show results of the SWC lead measurement for, respectively, a bulk gold electrode, a colloidal gold modified carbon electrode, and a colloidal gold mixed with poly(ester-sulfonic acid) polymer modified carbon electrode. In these graphs the stripping signals are expressed in units of charge density, i.e. $\mu C/cm^2$. These values were obtained by dividing the measured charge during the stripping scan by the active surface areas of the tested gold electrodes. The lead sensitivity of the colloidal gold modified carbon electrode (slope of FIG. 1) is approximately 5.6 times greater than the sensitivity of the bulk gold electrode (slope of FIG. 4). The lead sensitivity of the colloidal gold mixed with poly(ester-sulfonic acid) polymer modified carbon electrode (slope of FIG. 2) is approximately 14.5 times greater than the sensitivity of the colloidal gold modified carbon electrode (slope of FIG. 1) and 81 times greater than the sensitivity of the bulk gold electrode (slope of FIG. 4).

EXAMPLE 4

SWC Stripping Determination of lead in Urine

Synthetic urine is an aqueous solution of salts and organic compounds that mimics the chemical and physical properties of human urine. This product was purchased from CST Technologies, Inc. of Great Neck, N.Y. Five urine samples were tested. The samples were doped with lead to concentrations of 1.0 µg/dL, 2.0 µg/dL, 4.0 µg/dL, 8.0 µg/dL, and 16 µg/dL respectively. The doped lead values were confirmed by anodic stripping voltammetry.

Figure 5:
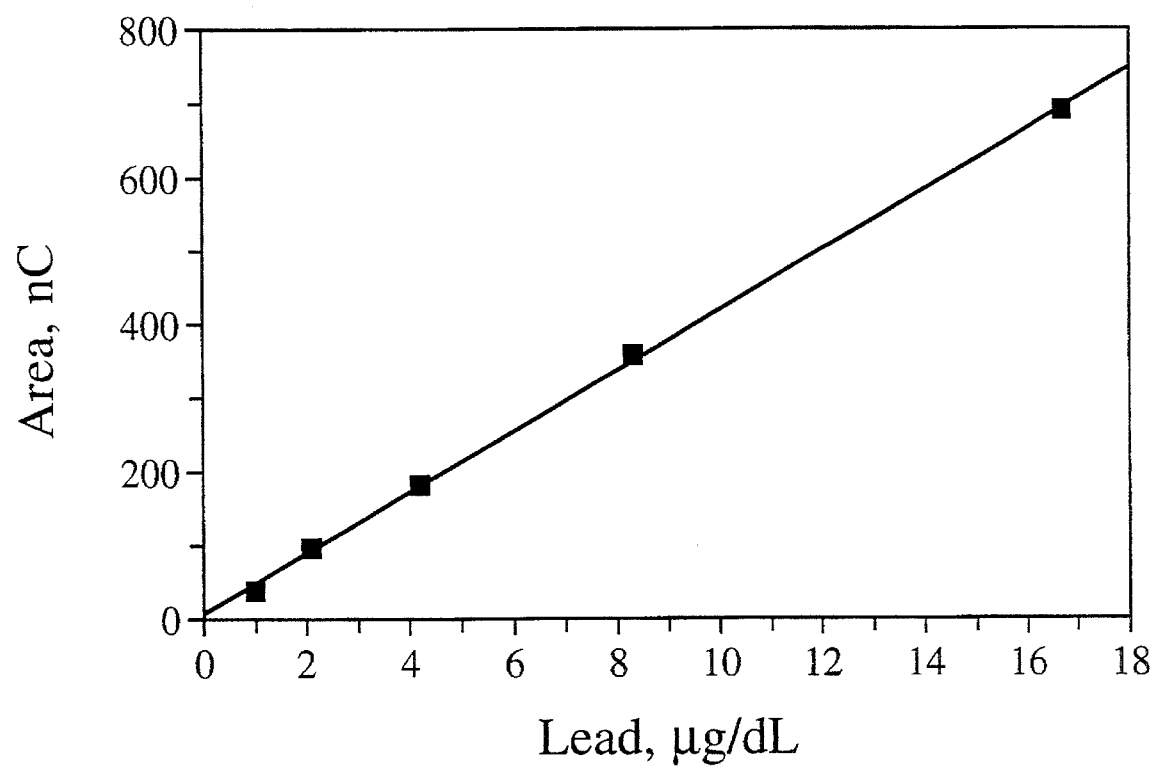
FIG. 5 is a graph showing the increasing charge, measured in nanocoulometers, with increasing lead ion concentration in synthetic urine. Lead concentrations are the lead concentrations at the time of analysis.

Carbon working electrodes were modified with 3 µL of 1 mg/mL 500 Å colloidal particles with 1% poly(ester-sulfonic acid) polymer as described in Example 1. Samples were pretreated with 100 mM HCl solutions. Sample (30–50 µL) was placed on the disposable 3-electrode sensor strip, described in Example 1, so as to cover all three electrodes within the circle of the insulating layer. The square wave coulometry (SWC) program was initiated within 10 seconds of application of the sample on the disposable sensor strip. Execution of the measurement sequence was confirmed by the monitor reading "Test in Progress". Within approximately 2 min. the display showed a lead concentration. Results are shown graphically in FIG. 5.

The reusable electronic meter's microprocessor automatically executes the sequence described in Example 2.

EXAMPLE 5

This example illustrates the rapid and accurate determination of lead in blood samples. The inventors have discovered that pretreatment of blood samples to bring the pH below 1 without significant dilution is important in preventing polymerization and coagulation of blood components. A suitable pretreatment was achieved using 400 mM hydrochloric acid.

Preparation of blood:

Blood samples were analyzed shortly after being drawn; alternatively, they were refrigerated for several days before analysis. For longer storage (e.g., longer than a week) blood samples were frozen. Frozen blood samples including those used as blood lead reference materials (e.g., Centers for Disease Control standards), should be thawed and allowed to stand at least 30 minutes at room temperature before analysis.

Three volumes of 400 mM HCl solution was added to 1 volume of blood in a disposable 1.5 mL microcentrifuge tube. The tube was capped and immediately stirred vigorously by turning the tube upside-down at least 5 times with tapping between turns. After 5 minutes the amount of lead in the sample was determined using square wave coulometry as described in Example 2.

EXAMPLE 6

Anodic Stripping Determination of lead in Blood

Three different blood samples were tested with disclosed lead sensor system, bovine blood lead control samples prepared by the CDC, freshly drawn human blood, and three commercially available whole human blood lead control samples obtained from UTAK Labs, Inc. (Valencia, Calif.).

The CDC bovine samples contain ingested lead and were sent with target values. The freshly drawn human blood was spiked with lead after taking the blood sample. The UTAK human control samples were doped with lead and had assigned lead concentrations of 9 µg/dL, 22 µg/dL and 34 µg/dL respectively, The CDC and UTAK assigned values were confirmed by graphite furnace atomic absorption spectrometry and anodic stripping voltammetry. The freshly drawn human blood values were confirmed by anodic stripping voltammetry.

Figure 6:
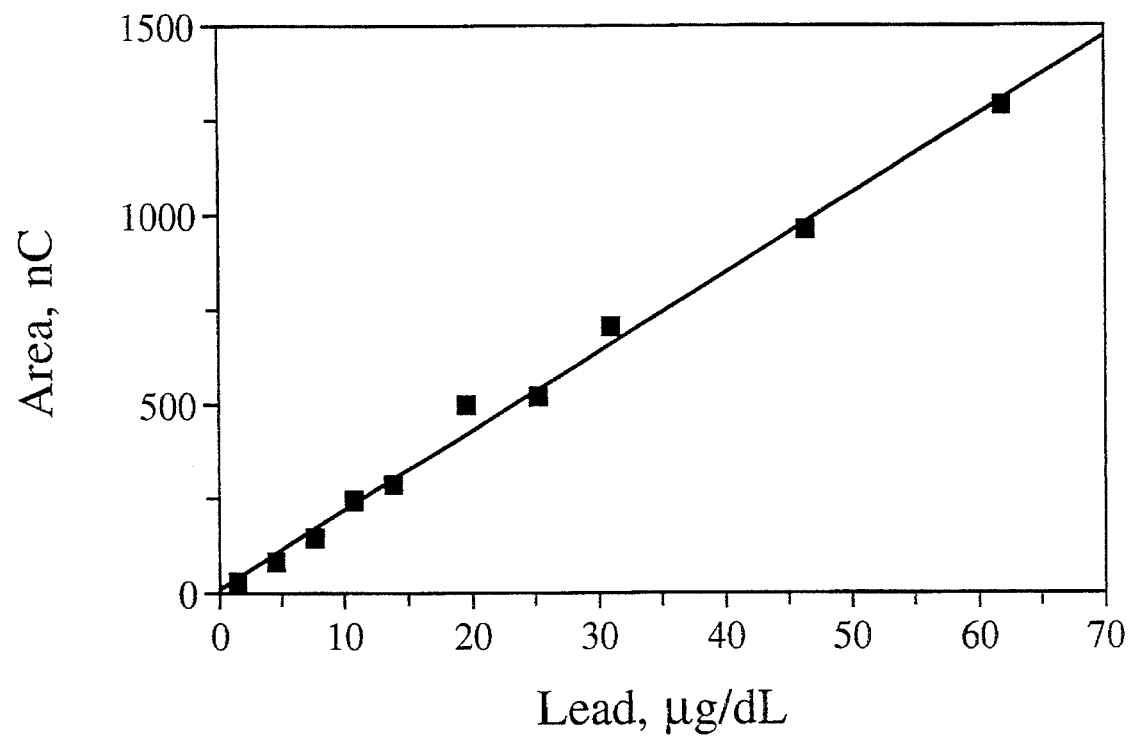
FIG. 6 is a graph showing the increasing charge, measured in nanocoulometers, with increasing lead ion concentration in bovine blood standards prepared by the U.S. Centers for Disease Control. The blood samples were acidified prior to placement on the colloidal gold modified electrodes. Lead concentrations are the lead concentrations of the samples before acid treatment.
Figure 7:
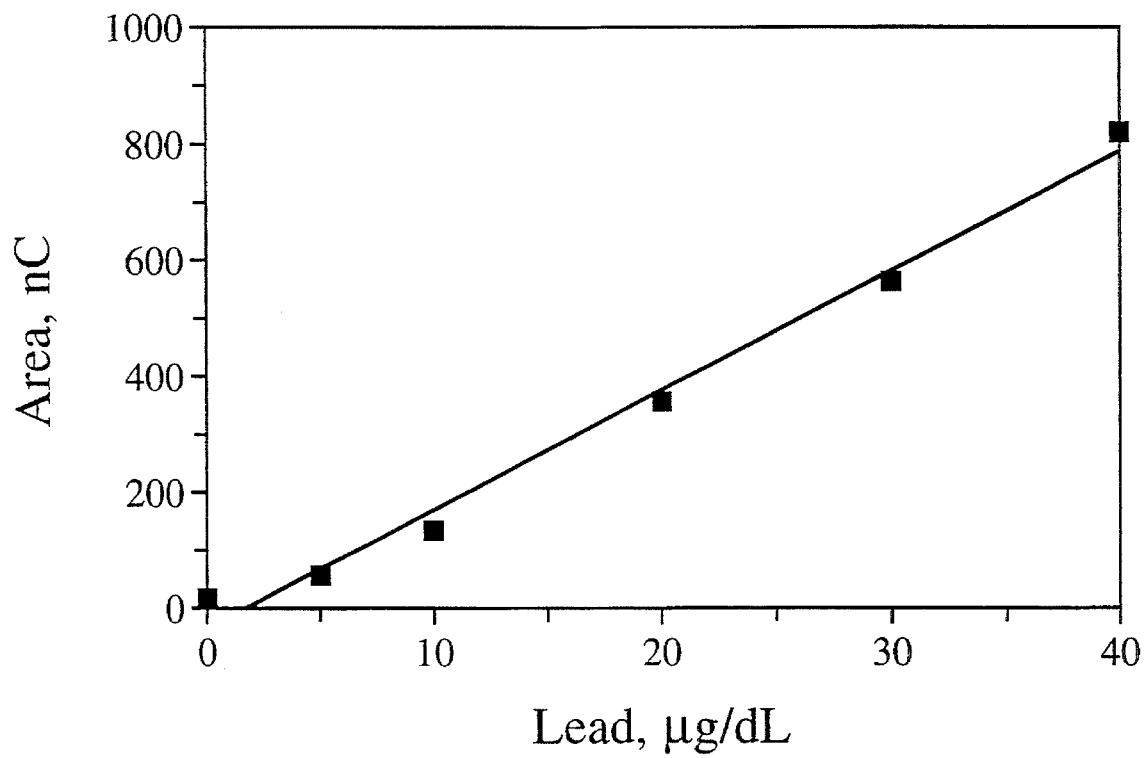
FIG. 7 is a graph showing the increasing charge, measured in nanocoulometers, with increasing lead ion concentration in freshly drawn human blood. The blood samples were acidified prior to placement on the colloidal gold modified electrodes. Lead concentrations are the lead concentrations of the samples before acid treatment.
Figure 8:
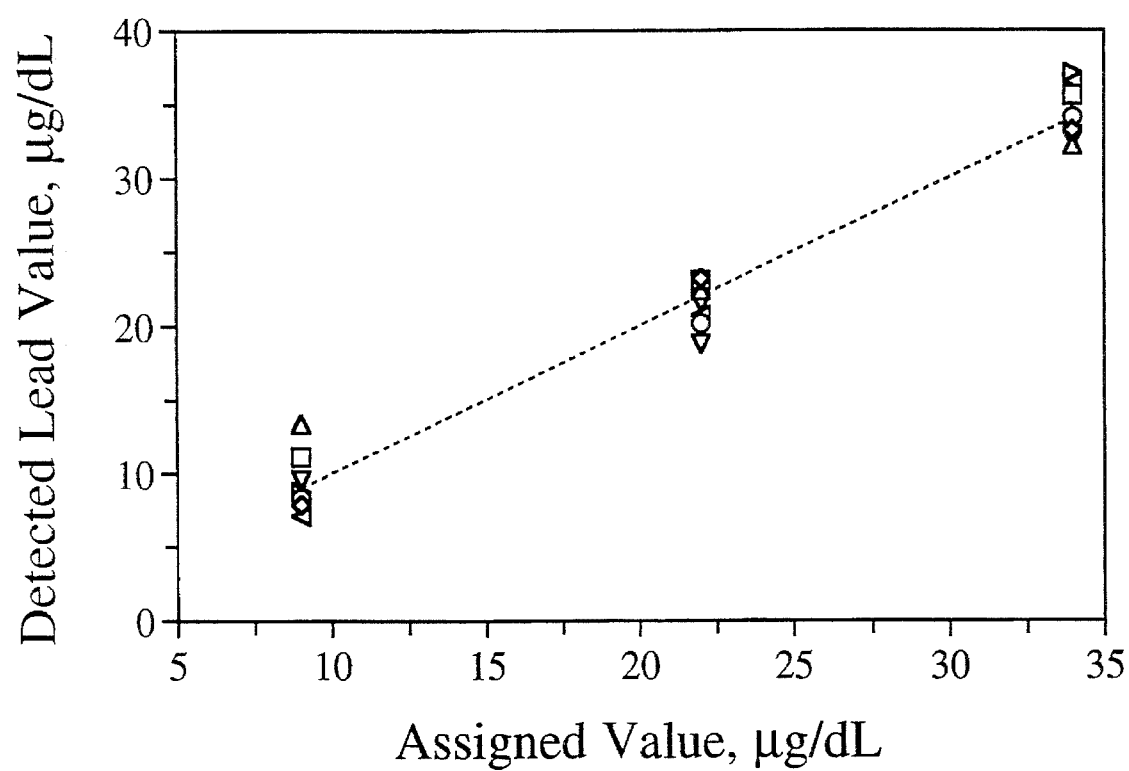
FIG. 8 is a graph showing nine detected lead values for each of three different human blood lead control samples measured with colloidal gold mixed with poly(ester-sulfonic acid) polymer modified carbon electrodes compared to the assigned values of 9 µg/dL, 22 µg/dL, and 34 µg/dL (represented by the dotted line).

The carbon working electrode was modified with 3 µL of 1 mg/mL 200 Å colloidal gold particles with 0.5% poly(ester-sulfonic acid) polymer as described in Example 1. Blood samples were pretreated with HCl solution as described in Example 5. Blood (30–50 µL) was placed on the disposable 3-electrode sensor strip, described in Example 1, so as to cover all three electrodes within the circle of the insulating layer. The square wave coulometry (SWC) program was initiated within 10 seconds of application of the sample on the disposable sensor strip. Execution of the measurement sequence was confirmed by the Monitor reading "Test in Progress". Within approximately 2 min. the display showed a lead reading. Results for the bovine blood samples are shown graphically in FIG. 6. Results for the freshly drawn human blood samples are shown graphically in FIG. 7. Results for the UTAK human control blood samples are shown graphically in FIG. 8.

The reusable electronic meter's microprocessor automatically executes the sequence described in Example 2.

EXAMPLE 7

This example illustrates the rapid and accurate determination of lead in blood samples with 500 Å colloidal gold particles deposited on screen printed carbon electrodes covered with a woven screen mesh. The inventors have found that a hydrophilic material covering the three electrode sensor, such as described in Example 1 facilitates the rapid and uniform distribution of a blood sample over the desired area. A suitable hydrophilic material is a polyester monofilament fabric purchased from Tetko, Inc. (Briarcliff Manor, N.Y.).

Figure 9:
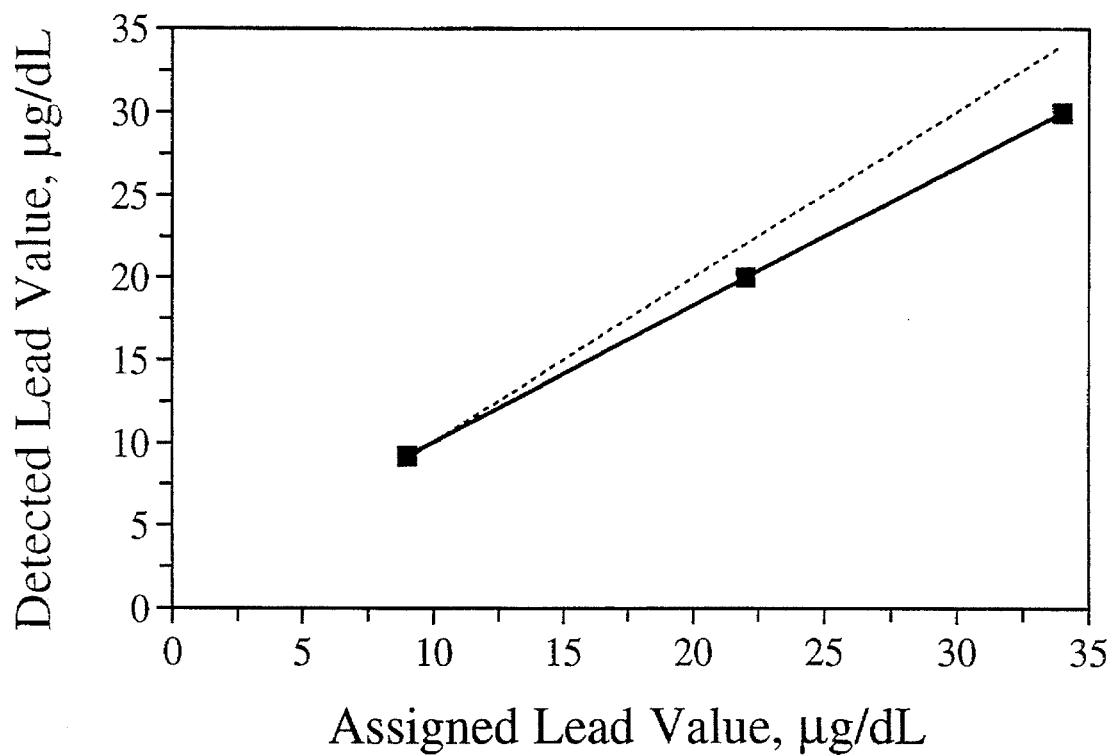
FIG. 9 is a graph showing the detected lead values of three different human blood lead control samples measured with a colloidal gold modified carbon electrode covered with a hydrophilic mesh compared to the assigned values of 9 µg/dL, 22 µg/dL, and 34 µg/dL (represented by the dotted line).

A colloidal gold modified carbon electrode was fabricated as described in Example 1 with 500 Å colloidal gold particles. A woven screen mesh of polyester monofilament fabric was affixed over the sample placement area of the working electrode, reference electrode, and counter electrode. Mesh covered colloidal gold modified electrodes were used to test three different blood lead control materials purchased from UTAK Labs, Inc. (Valencia, Calif.) that were acid treated as described in Example 5. These electrodes measured lead values for these control samples that were on average within 7.8% of their assigned lead values. Representative data are shown in FIG. 9.

A reusable electronic meter's microprocessor automatically executed the sequence described in Example 2.

EXAMPLE 8

This example illustrates certain electrochemical properties of the colloidal gold modified electrodes developed by the inventors. The colloidal gold modified electrodes act as a microelectrode array. For the same geometric area, the stripping detection signal of a microelectrode array is greater than the stripping detection signal for a planar electrode.

The response of microelectrode arrays has three regimes of scanning frequency dependence. The divisions between the regimes depends on the analyte diffusion distance relative to the radius of the individual microelectrodes and the separation between the individual microelectrodes. In high frequency scans, analyte diffusion distance is small compared to microelectrode radius. Signal is limited by the aggregate area of the microelectrodes and is proportional to the square root of frequency. In low frequency scans, analyte diffusion distances to the individual microelectrodes overlap. Signal is limited by the macroscopic geometric area of the array and is proportional to the square root of frequency. In between frequency scan extremes analyte diffusion distances are not small compared to microelectrode radius but do not overlap the individual microelectrodes. Signal response is in a steady-state and essentially is independent of frequency.

Signal response exhibits mixed behavior at the boundaries of these regions. The frequency positions of the boundaries give information about the average microelectrode radius and the average distance of separation of the microelectrodes. At a frequency of 1 Hz the disclosed colloidal gold modified electrode exhibited a steady-state response to 1 ppm lead that extends at least from 0.5 to 2 Hz. Exploration of the steady state frequency boundaries of the disclosed colloidal gold modified electrodes provided an to estimate of microelectrode size (radius=$1.5\times10^{-3}$ cm), microelectrode number ($9\times10^4$), and distance of separation of the microelectrodes ($1.2\times10^{-3}$). The sensitivity of the electrode under the instrumental conditions used in this example is represented by:

Signal response=(104[concentration of sample lead])+1 where $R^2$=0.994.

After correction for geometric areas, the relative signal response of colloidal gold modified carbon electrodes in unstirred samples was $\geq2$ the relative signal response of bulk gold electrodes in unstirred samples.

Additional evidence to support the microelectrode array behavior of the disclosed colloidal gold modified carbon electrode was obtained by examining the dependence between the SWC signal and the deposition time in the absence of forced convection, e.g. stirring. The SWC signal for blood lead, or the stripping peak current, increased in proportion to the increase of the deposition time. This linear dependence proved the nonlinear diffusion pattern of the transport of lead ions to the electrode surface during the deposition step, which is characteristic of the microelectrode array behavior. A square root dependence between the signal and the deposition time would be expected for a macroelectrode in a quiescent solution. Furthermore, it was observed that under the conditions of relatively fast SWV the disclosed colloidal gold modified carbon electrodes generated sigmoidal shaped forward and reverse current curves with a diffusion plateau well above that expected for a macroelectrode.

Forward and reverse current curves obtained in SWV stripping experiments involving lead and the disclosed colloidal gold modified electrodes, exhibit a sigmoidal-like shape with a diffusion plateau well above. This shows that under the conditions of relatively fast SWV the disclosed electrodes acted as a microelectrode array.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Biberian, J. P. and Rhead, G. E. (1973) *J. Phys. F (Metal Phys.)*, 3, 675.
Copeland, T. R. and Skogerboe, R. K. (1974) *Anal. Chem.*, 46, 1257A.
Hamelin, A. (1979) *J. Electroanal. Chem.*, 101, 285–290.
Housberger, M. in Scanning Electron Microscopy, 2, 9, 1981
Lord Jr., S. S., O'Neill, R. C., and Rogers, L. B. (1952) *Anal. Chem.*, 24, 209–213.
Moremans, M., Daneels, G. and DeMay, J. Sensitive colloidal metal (gold or silver) staining of protein blots on nitrocellulose membranes. *Anal. Biochem.*, 145, 315–321, (1985).
Nicholson, M. M. (1957) *Anal. Chem.*, 32, 1058–1062.
Nicholson, M. M. (1960) *J. Am. Chem. Soc.*, 79, 7–12.
Perdereau, J., Biberian, J. P. and Rhead, G. E. (1974) *J. Phys. F (Metal Phys.)*, 4, 798.
Posey, R. and Andrew, R. (1980) *Anal. Chim. Acta*, 119, 55.
Sawyer, D. T. and Roberts, Jr., J. L. "Experimental Electrochemistry for Chemists," Wiley, 1974
Wang, J. and Tian, B. (1993) *Anal. Chem.*, 65, 1529–1532.
Wang, J., Stripping Analysis: *Principles, Instrumentation, and Applications*; VCH Publishers; Deerfield Beach, Fla., 1985.
Wojciechowski, M.; Balcerzak, J. Square-Wave Anodic Stripping Voltammetry at Glassy-Carbon-Based Thin Mercury Film Electrodes in Solutions Containing Dissolved Oxygen. *Anal. Chem.*, 62, 1325–1331, (1990).

What is claimed is:

1. An electrode comprising a conducting substrate onto which is deposited 10–30 µg/cm$^2$ of colloidal gold admixed with a cationic polymer.

2. The electrode of claim 1 wherein the cationic polymer is a poly(ester-sulfonic acid).

3. The electrode of claim 1 wherein the conducting substrate is glassy carbon.

4. The electrode of claim 1 wherein the conducting substrate is carbon ink.

5. The electrode of claim 4, wherein the electrode is screen printed.

6. An electrode comprising colloidal gold dispersed in a cationic polymer matrix that is deposited onto an electrode surface to form a microelectrode array.

7. The microelectrode array of claim 6 wherein the cationic polymer is poly(ester-sulfonic acid).

8. The microelectrode array of claim 6 wherein the electrode surface is screen printed carbon ink or glassy carbon.

9. The microelectrode array of claim 6 wherein size of the colloidal gold is between about 200 and 500 angstroms in diameter.

10. A lead monitoring device comprising the electrode of claim 1 or claim 6, a reference electrode, a counter electrode coupled, means of measuring current, and means for performing square wave coulometric analysis.

11. A method of determining lead ion levels, comprising the steps:
    contacting a sample suspected of containing lead ion with the electrode of claim 1 or the microelectrode array of claim 6;
    reductively plating metallic lead onto the electrode surface;
    stripping the plated lead from the electrode surface to form lead ion to produce a current; and
    relating amount of current generated to the lead ion level in the sample.

12. The method of claim 11 wherein the sample is a water sample or a urine sample.

13. The method of claim 11 wherein the sample is a blood sample.

14. The method of claim 13 wherein the blood sample is admixed with an acid prior to the contacting step.

15. The method of claim 11 wherein current is determined by square wave coulometry.

16. The method of claim 11 wherein the sample volume is between 10 and 100 µL.

17. The method of claim 11 wherein the reductive plating is accomplished at about −0.5 volts.

18. The method of claim 11 wherein the stripping is by square wave voltammetry in a potential range between −0.5 and +0.5 volts.

19. A system for coulometric determination of heavy metal ions that have a stripping potential between −0.5 and +1.0 volts, comprising the electrode of claim 6, a coupled working electrode and means for adjusting deposition potential between about −0.5 and +0.5 volts.

20. A method of determining blood lead ion levels in the range of about 1 to about 60 µg/dL comprising:
    admixing acid with a blood sample suspected of containing lead;
    reductively depositing the lead onto the coupled electrode of claim 6 at a potential of about −0.5 volts; and
    coulometrically determining the amount of deposited lead.

21. An electrode comprising a carbon ink substrate onto which is deposited a film consisting essentially of colloidal gold particles having a size of about 200–500 Å admixed with a poly(ester-sulfonic acid) polymer.

22. The electrode of claim 21, wherein the electrode is screen printed.

* * * * *